US012201476B2

(12) United States Patent
Karasawa

(10) Patent No.: US 12,201,476 B2
(45) Date of Patent: Jan. 21, 2025

(54) ULTRASOUND SYSTEM AND METHOD FOR CONTROLLING ULTRASOUND SYSTEM

(71) Applicant: FUJIFILM Corporation, Tokyo (JP)

(72) Inventor: Hiroyuki Karasawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/300,213

(22) Filed: Apr. 13, 2023

(65) Prior Publication Data
US 2023/0248335 A1 Aug. 10, 2023

Related U.S. Application Data

(60) Division of application No. 17/065,115, filed on Oct. 7, 2020, now Pat. No. 11,690,596, which is a
(Continued)

(30) Foreign Application Priority Data

Apr. 13, 2018 (JP) ................. 2018-077886

(51) Int. Cl.
A61B 8/15 (2006.01)
A61B 8/00 (2006.01)
A61B 8/08 (2006.01)

(52) U.S. Cl.
CPC ............. A61B 8/4472 (2013.01); A61B 8/15 (2013.01); A61B 8/4494 (2013.01); A61B 8/461 (2013.01); A61B 8/5215 (2013.01); A61B 8/56 (2013.01)

(58) Field of Classification Search
CPC ........... A61B 8/14; A61B 8/15; A61B 8/4472; A61B 8/4494; A61B 8/461; A61B 8/5215;
(Continued)

(56) References Cited

U.S. PATENT DOCUMENTS 7,909,764 B1 3/2011 Wenzel et al.
11,690,596 B2 7/2023 Karasawa
(Continued)

FOREIGN PATENT DOCUMENTS

CN 1494873 A 5/2004
CN 101143101 A 3/2008
(Continued)

OTHER PUBLICATIONS

An Office Action; "Notice of Reasons for Refusal," mailed by the Japanese Patent Office on Aug. 29, 2023, which corresponds to Japanese Patent Application No. 2023-010040 and is related to U.S. Appl. No. 18/300,213; with English language translation.
(Continued)

Primary Examiner — Chao Sheng
Assistant Examiner — Maria Christina Talty
(74) Attorney, Agent, or Firm — Studebaker & Brackett PC

(57) ABSTRACT

Provided is an ultrasound system including an ultrasound probe and an image display device. The ultrasound probe includes: a transducer array, a transmitting and receiving unit that generates a sound ray signal on the basis of a reception signal from the transducer array; an image information data generation unit that generates image information data from the sound ray signal; and a probe-side wireless communication unit that transmits the image information data to the image display device. The image display device includes: an operating state acquisition unit that acquires an operating state of the image display device; and a display-device-side wireless communication unit that transmits the operating state to the ultrasound probe. The ultrasound probe includes at least one of an ultrasound transmission and reception control unit that controls transmission and reception of the ultrasonic waves on the basis of
(Continued)

the operating state of the image display device or an output format setting unit that sets an output format of the image information data on the basis of the operating state of the image display device.

16 Claims, 4 Drawing Sheets

Related U.S. Application Data continuation of application No. PCT/JP2019/015746, filed on Apr. 11, 2019.

(58) Field of Classification Search
CPC ..... A61B 8/56; G01S 15/899; G01S 7/52053; G01S 7/5208

See application file for complete search history.

(56) References Cited

U.S. PATENT DOCUMENTS

| | | | |
|---|---|---|---|
| 2004/0019270 | A1 | 1/2004 | Takeuchi |
| 2008/0064955 | A1 | 3/2008 | Miyajima |
| 2008/0114255 | A1 | 5/2008 | Schwartz et al. |
| 2011/0061466 | A1* | 3/2011 | Nishino ............... A61B 8/461 73/632 |
| 2012/0232397 | A1* | 9/2012 | Ohshima ............ G01S 7/52084 600/443 |
| 2012/0316443 | A1 | 12/2012 | Katou |
| 2013/0060142 | A1* | 3/2013 | Ishihara ................ A61B 8/14 600/447 |
| 2013/0079638 | A1 | 3/2013 | Osawa |
| 2014/0148698 | A1* | 5/2014 | Tamano ............. G01S 7/52042 600/438 |
| 2014/0148699 | A1* | 5/2014 | Shim ..................... A61B 8/488 600/443 |
| 2014/0300720 | A1 | 10/2014 | Rothberg |
| 2016/0066893 | A1 | 3/2016 | Cho et al. |
| 2016/0278739 | A1 | 9/2016 | Pelissier et al. |
| 2017/0035390 | A1 | 2/2017 | Ryu et al. |
| 2017/0100098 | A1 | 4/2017 | Urabe et al. |
| 2017/0128046 | A1 | 5/2017 | Kim et al. |
| 2019/0008486 | A1* | 1/2019 | Jin ....................... A61B 8/4444 |

FOREIGN PATENT DOCUMENTS

| | | | |
|---|---|---|---|
| CN | 104434192 | A | 3/2015 |
| CN | 105263419 | A | 1/2016 |
| CN | 106255463 | A | 12/2016 |
| CN | 106923863 | A | 7/2017 |
| JP | 2011-087698 | A | 5/2011 |
| JP | 2012245021 | A * | 12/2012 |
| JP | 2013-090827 | A | 5/2013 |
| JP | 2014-050648 | A | 3/2014 |
| JP | 2015-211726 | A | 11/2015 |
| JP | 2016-209569 | A | 12/2016 |
| JP | 2017-511732 | A | 4/2017 |
| JP | 2017099785 | A * | 6/2017 |
| JP | 7219761 | B2 | 2/2023 |
| WO | 2008/146208 | A2 | 12/2008 |
| WO | 2014/165662 | A2 | 10/2014 |

OTHER PUBLICATIONS

An Office Action mailed by China National Intellectual Property Administration on Mar. 23, 2023, which corresponds to Chinese Patent Application No. 201980025317.1 and is related to U.S. Appl. No. 18/300,213; with partial English translation.

International Search Report issued in PCT/JP2019/015746; mailed Jun. 25, 2019.

International Preliminary Report On Patentability and Written Opinion issued in PCT/JP2019/015746; issued Oct. 13, 2020.

The extended European search report issued by the European Patent Office on May 6, 2021, which corresponds to European Patent Application No. 19785265.0-1126 and is related to U.S. Appl. No. 17/065,115.

An Office Action; "Notice of Reasons for Refusal," mailed by the Japanese Patent Office on Nov. 24, 2021, which corresponds to Japanese Patent Application No. 2020-513446 and is related to U.S. Appl. No. 17/065,115 with English translation.

An Office Action; "Notice of Reasons for Refusal", mailed by the Japanese Patent Office on Apr. 12, 2022, which corresponds to Japanese Patent Application No. 2020-513446 and is related to U.S. Appl. No. 17/065,115; with English language translation.

"Notice of Reasons for Refusal" Office Action issued in JP 2020-513446; mailed by the Japanese Patent Office on Sep. 13, 2022.

An Office Action; "Notice of Reasons for Refusal," mailed by the Japanese Patent Office on Aug. 6, 2024, which corresponds to Japanese Patent Application No. 2023-195149 and is related to U.S. Appl. No. 18/300,213; with English language translation.

* cited by examiner

ULTRASOUND SYSTEM AND METHOD FOR CONTROLLING ULTRASOUND SYSTEM

CROSS-REFERENCE TO RELATED APPLICATIONS

This application is a Divisional of U.S. patent application Ser. No. 17/065,115 filed on Oct. 7, 2020, which is a Continuation of PCT International Application No. PCT/JP2019/015746 filed on Apr. 11, 2019, which claims priority under 35 U.S.C. § 119(a) to Japanese Patent Application No. 2018-077886 filed on Apr. 13, 2018. Each of the above applications is hereby expressly incorporated by reference, in its entirety, into the present application.

BACKGROUND OF THE INVENTION

1. Field of the Invention

The present invention relates to an ultrasound system and a method for controlling the ultrasound system, and more particularly, to an ultrasound system in which an ultrasound probe and an image display device are connected by wireless communication and a method for controlling the ultrasound system.

2. Description of the Related Art

In the related art, an ultrasound diagnostic apparatus using an ultrasound image has been put to practical use in the medical field. In general, this type of ultrasound diagnostic apparatus includes an ultrasound probe having a transducer array provided therein and an apparatus main body connected to the ultrasound probe. Ultrasonic waves are transmitted from the ultrasound probe to a subject. The ultrasound probe receives ultrasound echoes from the subject. The apparatus main body electrically processes a reception signal to generate an ultrasound image.

In recent years, for example, as disclosed in JP2015-211726A, an ultrasound system has been developed in which an ultrasound probe and an apparatus main body are connected by wireless communication to improve the operability and mobility of the ultrasound probe.

In the wireless ultrasound system, a reception signal output from the transducer array of the ultrasound probe is transmitted to the apparatus main body by wireless communication. Alternatively, a circuit for signal processing is provided in the ultrasound probe and the ultrasound probe performs digital processing on the reception signal output from the transducer array and transmits the reception signal to the apparatus main body using wireless communication. The apparatus main body generates an ultrasound image. The ultrasound image generated in this way is displayed at a predetermined display frame rate by the apparatus main body.

SUMMARY OF THE INVENTION

In general, in a case in which the temperature of the apparatus main body is equal to or greater than a predetermined temperature, it may be difficult for a circuit, a display unit, and the like included in the apparatus main body to function normally. In this case, the processing capability of the apparatus main body is generally reduced to prevent an increase in the temperature of the apparatus main body. In a case in which the processing capability of the apparatus main body is reduced in this way, a large amount of processing time is required to generate an ultrasound image and to display the generated ultrasound image in the apparatus main body. Therefore, the processing of the signal transmitted from the ultrasound probe by wireless communication may be delayed and it may be difficult to normally display the ultrasound image.

In addition, the amount of data of the ultrasound image that can be normally displayed on the display unit varies depending on, for example, the resolution of the display unit in the apparatus main body, the refresh rate of the display unit, and a wireless communication state between the ultrasound probe and the apparatus main body. Therefore, the processing of the signal transmitted from the ultrasound probe by wireless communication may be delayed and it may be difficult to normally display the ultrasound image.

The invention has been made in order to solve the problems of the related art and an object of the invention is to provide an ultrasound system that can normally display an ultrasound image regardless of the operating state of an apparatus main body, such as processing capability, and a method for controlling the ultrasound system.

In order to achieve the above object, an ultrasound system according to the invention comprises an ultrasound probe and an image display device. The ultrasound probe includes: a transducer array; a transmitting and receiving unit that transmits ultrasonic waves from the transducer array and generates a sound ray signal on the basis of a reception signal acquired by the transducer array; an image information data generation unit that generates image information data on the basis of the sound ray signal generated by the transmitting and receiving unit; and a probe-side wireless communication unit that wirelessly transmits the image information data generated by the image information data generation unit to the image display device. The image display device includes: a display unit that displays an ultrasound image on the basis of the image information data wirelessly transmitted from the ultrasound probe; an operating state acquisition unit that acquires an operating state of the image display device; and a display-device-side wireless communication unit that wirelessly transmits the operating state of the image display device acquired by the operating state acquisition unit to the ultrasound probe. The ultrasound probe includes at least one of an ultrasound transmission and reception control unit that controls transmission and reception of the ultrasonic waves by the transmitting and receiving unit on the basis of ultrasound transmission and reception conditions corresponding to the operating state of the image display device wirelessly transmitted from the image display device or an output format setting unit that sets an output format of the image information data wirelessly transmitted from the ultrasound probe to the image display device on the basis of the operating state of the image display device wirelessly transmitted from the image display device.

Preferably, the image display device has a processor including a central processing unit, and the operating state of the image display device is at least one of a configuration of the central processing unit, a clock frequency of the central processing unit, a resolution of the display unit, or a refresh rate of the display unit.

In this case, preferably, the image display device includes a temperature sensor and a clock control unit that controls the clock frequency of the central processing unit according to a temperature detected by the temperature sensor, and the operating state of the image display device is the clock frequency of the central processing unit controlled by the clock control unit.

Alternatively, preferably, the image display device includes a communication state detection unit that detects a wireless communication state between the ultrasound probe and the image display device, and the operating state of the image display device is the wireless communication state detected by the communication state detection unit.

In this case, the image display device may include a display frame rate determination unit that determines a display frame rate on the basis of at least the wireless communication state, and the display unit may display the ultrasound image on the basis of the display frame rate determined by the display frame rate determination unit.

The image display device may include a safety evaluation index calculation unit that calculates a safety evaluation index on the basis of ultrasound transmission and reception conditions controlled by the ultrasound transmission and reception control unit of the ultrasound probe and displays the safety evaluation index on the display unit. The ultrasound probe may wirelessly transmit, to the image display device, a notification that the transmission and reception of the ultrasonic waves by the transmitting and receiving unit are controlled on the basis of the ultrasound transmission and reception conditions corresponding to the operating state of the image display device wirelessly transmitted from the image display device. The safety evaluation index calculation unit may calculate the safety evaluation index and display the safety evaluation index on the display unit after receiving the notification wirelessly transmitted from the ultrasound probe.

Preferably, the image information data is a signal obtained by performing attenuation correction according to a depth of a reflection position of the ultrasonic waves and an envelope detection process on the sound ray signal generated by the transmitting and receiving unit.

In addition, the image information data may be an ultrasound image signal obtained by performing attenuation correction according to a depth of a reflection position of the ultrasonic waves and an envelope detection process on the sound ray signal generated by the transmitting and receiving unit and converting the sound ray signal according to a predetermined image display method.

Preferably, the transmitting and receiving unit includes: a transmitting unit that directs the transducer array to transmit the ultrasonic waves; and a receiving unit that generates the sound ray signal on the basis of the reception signal acquired by the transducer array.

According to the invention, there is provided a method of controlling an ultrasound system comprising an ultrasound probe and an image display device. The method comprises: generating a sound ray signal by directing a transducer array of the ultrasound probe to transmit and receive ultrasonic waves; generating image information data on the basis of the generated sound ray signal; wirelessly transmitting the generated image information data from the ultrasound probe to the image display device; displaying an ultrasound image on a display unit of the image display device on the basis of the image information data wirelessly transmitted from the ultrasound probe; wirelessly transmitting an operating state of the image display device from the image display device to the ultrasound probe; and allowing the ultrasound probe to perform at least one of control of the transmission and reception of the ultrasonic waves on the basis of ultrasound transmission and reception conditions corresponding to the operating state of the image display device wirelessly transmitted from the image display device or setting of an output format of the image information data wirelessly transmitted to the image display device on the basis of the operating state of the image display device wirelessly transmitted from the image display device.

According to the invention, the ultrasound probe comprises at least one of the ultrasound transmission and reception control unit that controls the transmission and reception of the ultrasonic waves by the transmitting and receiving unit on the basis of the ultrasound transmission and reception conditions corresponding to the operating state of the image display device wirelessly transmitted from the image display device or the output format setting unit that sets the output format of the image information data wirelessly transmitted from the ultrasound probe to the image display device on the basis of the operating state of the image display device wirelessly transmitted from the image display device. Therefore, it is possible to normally display an ultrasound image regardless of the operating state of the image display device.

DESCRIPTION OF THE PREFERRED EMBODIMENTS

Embodiments of the invention will be described below with reference to the accompanying drawings.

Embodiment 1

Figure 1:
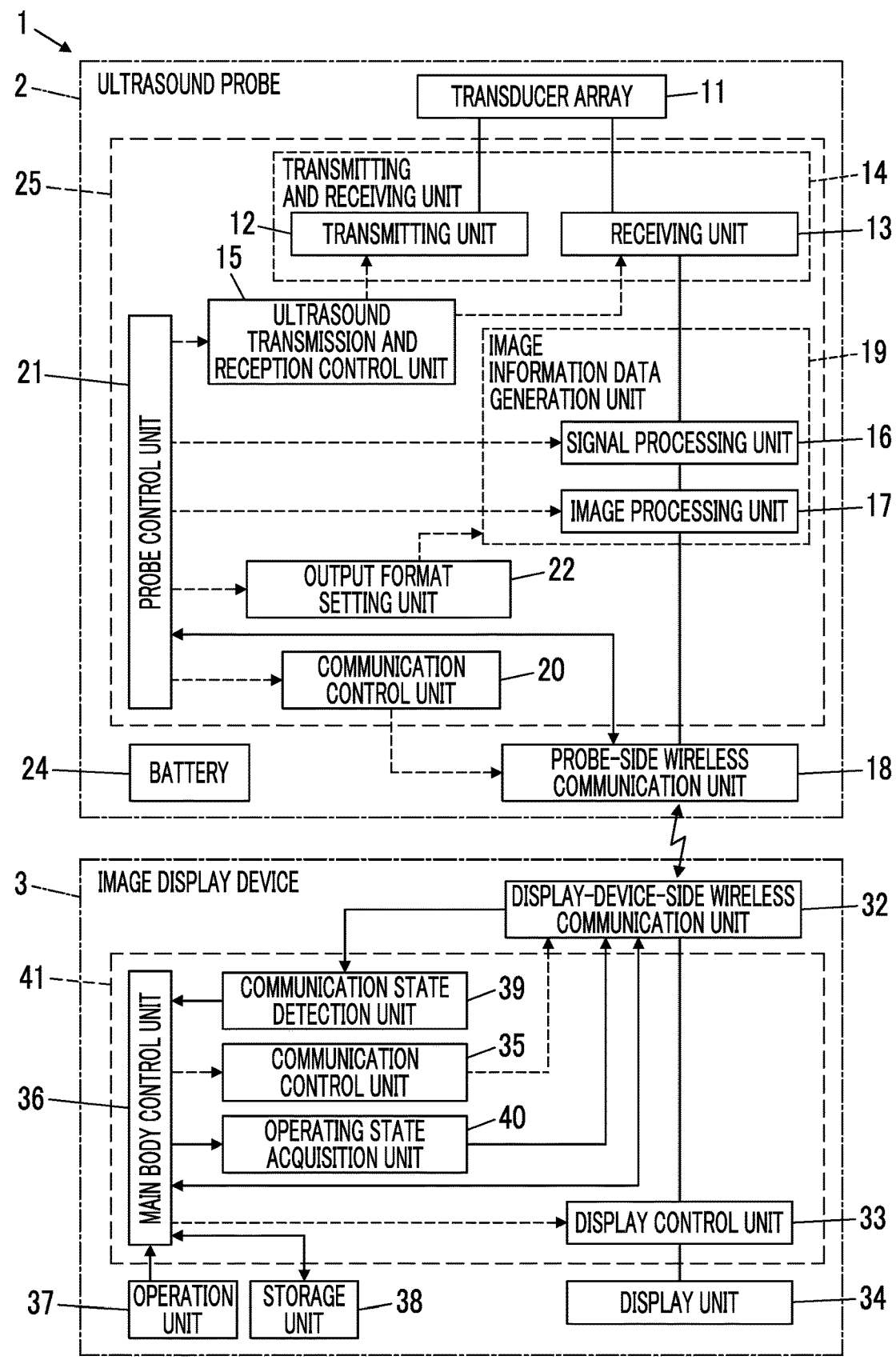
FIG. 1 is a block diagram illustrating a configuration of an ultrasound system according to Embodiment 1 of the invention.

FIG. 1 illustrates the configuration of an ultrasound system 1 according to Embodiment 1 of the invention. As illustrated in FIG. 1, the ultrasound system 1 comprises an ultrasound probe 2 and an image display device 3. The ultrasound probe 2 and the image display device 3 are connected by wireless communication.

The ultrasound probe 2 of the ultrasound system 1 comprises a transducer array 11. The transducer array 11 is connected to a transmitting unit 12 and a receiving unit 13. The transmitting unit 12 and the receiving unit 13 form a transmitting and receiving unit 14. An ultrasound transmission and reception control unit 15 is connected to the transmitting unit 12 and the receiving unit 13. A signal processing unit 16, an image processing unit 17, and a probe-side wireless communication unit 18 are sequentially connected to the receiving unit 13. The signal processing unit 16 and the image processing unit 17 form an image information data generation unit 19.

In addition, a communication control unit 20 is connected to the probe-side wireless communication unit 18, and an output format setting unit 22 is connected to the image information data generation unit 19. Further, a probe control unit 21 is connected to the ultrasound transmission and reception control unit 15, the signal processing unit 16, the image processing unit 17, the communication control unit 20, and the output format setting unit 22. Further, the ultrasound probe 2 has a battery 24 provided therein.

A probe-side processor 25 is configured by the transmitting unit 12, the receiving unit 13, the ultrasound transmission and reception control unit 15, the signal processing unit 16, the image processing unit 17, the communication control unit 20, the probe control unit 21, and the output format setting unit 22.

The image display device 3 of the ultrasound system 1 comprises a display-device-side wireless communication unit 32. A display control unit 33 and a display unit 34 are sequentially connected to the display-device-side wireless communication unit 32. Further, a communication control unit 35, a communication state detection unit 39, and an operating state acquisition unit 40 are connected to the display-device-side wireless communication unit 32. Furthermore, a main body control unit 36 is connected to the display control unit 33, the communication control unit 35, the communication state detection unit 39, and the operating state acquisition unit 40. An operation unit 37 and a storage unit 38 are connected to the main body control unit 36. The display-device-side wireless communication unit 32 and the main body control unit 36 are connected such that information can be bidirectionally received and transmitted. The main body control unit 36 and the storage unit 38 are connected such that information can be bidirectionally received and transmitted.

Furthermore, a display-device-side processor 41 is configured by the display control unit 33, the communication control unit 35, the main body control unit 36, the communication state detection unit 39, and the operating state acquisition unit 40.

Further, the probe-side wireless communication unit 18 of the ultrasound probe 2 and the display-device-side wireless communication unit 32 of the image display device 3 are connected such that information can be bidirectionally received and transmitted. Therefore, the ultrasound probe 2 and the image display device 3 are connected by wireless communication.

The transducer array 11 of the ultrasound probe 2 has a plurality of ultrasound transducers which are arranged one-dimensionally or two-dimensionally. Each of the transducers transmits ultrasonic waves according to a driving voltage signal supplied from the transmitting unit 12, receives waves reflected from a subject, and outputs a reception signal. Each transducer is configured using an element in which electrodes are formed at both ends of a piezoelectric body consisting of, for example, a piezoelectric ceramic typified by lead zirconate titanate (PZT), a polymeric piezoelectric element typified by polyvinylidene difluoride (PVDF), and a piezoelectric single crystal typified by lead magnesium niobate-lead titanate (PMN-PT).

The transmitting unit 12 of the transmitting and receiving unit 14 includes, for example, a plurality of pulse generators, adjusts the amount of delay of each driving signal on the basis of a transmission delay pattern selected according to a control signal from the ultrasound transmission and reception control unit 15 such that the ultrasonic waves transmitted from the plurality of transducers of the transducer array 11 form an ultrasound beam, and supplies the driving signals to the plurality of transducers. As such, in a case in which a pulsed or continuous-wave voltage is applied to the electrodes of the transducers of the transducer array 11, the piezoelectric body is expanded and contracted and pulsed or continuous ultrasonic waves are generated from each transducer. An ultrasound beam is formed from a combined wave of the ultrasonic waves.

The transmitted ultrasound beam is reflected by a target, such as a part of the subject, and is propagated toward the transducer array 11. The ultrasonic waves propagated toward the transducer array 11 in this way are received by each of the ultrasound transducers forming the transducer array 11. In this case, each of the ultrasound transducers forming the transducer array 11 receives propagated ultrasound echoes, is expanded and contracted to generate an electric signal, and outputs a reception signal which is the electric signal to the receiving unit 13.

Figure 2:
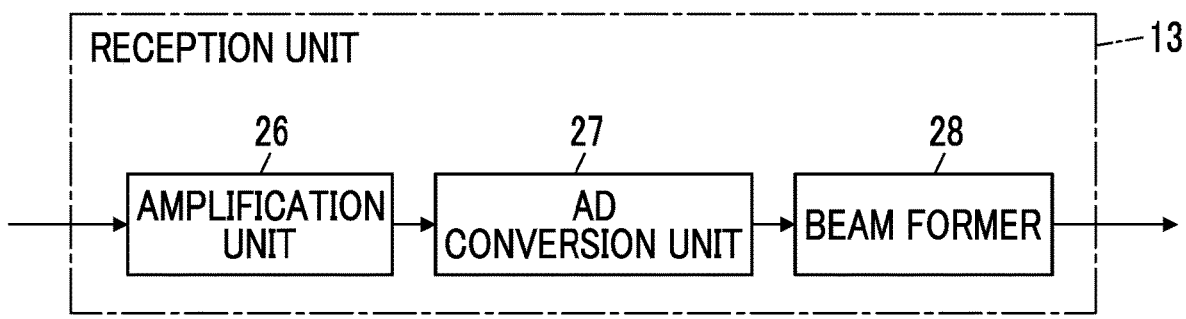
FIG. 2 is a block diagram illustrating an internal configuration of a receiving unit according to Embodiment 1 of the invention.

The receiving unit 13 of the transmitting and receiving unit 14 processes the reception signal output from the transducer array 11 according to a control signal from the ultrasound transmission and reception control unit 15. As illustrated in FIG. 2, the receiving unit 13 has a configuration in which an amplification unit 26, an analog digital (AD) conversion unit 27, and a beam former 28 are connected in series to each other. The amplification unit 26 amplifies the reception signal input from each of the transducers forming the transducer array 11 and transmits the amplified reception signal to the AD conversion unit 27. The AD conversion unit 27 converts the reception signal transmitted from the amplification unit 26 into digital element data and transmits the element data to the beam former 28. The beam former 28 performs a reception focusing process which gives a delay to each element data item following the set sound velocity on the basis of a reception delay pattern selected according to a control signal from the ultrasound transmission and reception control unit 15 and performs addition (phasing addition). The sound ray signal in which the focus of the ultrasound echo is narrowed is generated by the reception focusing process.

The ultrasound transmission and reception control unit 15 of the probe-side processor 25 controls the transmitting unit 12 and the receiving unit 13 of the transmitting and receiving unit 14 to perform the transmission of ultrasound beams and the reception of ultrasound echoes on the basis of an inspection mode and a scanning method instructed by the probe control unit 21. Here, it is assumed that the inspection mode indicates any one of the inspection modes that can be used in an ultrasound diagnostic apparatus, such as a brightness (B) mode, a color Doppler (CF) mode, a power Doppler (PD) mode, a pulse Doppler (PW) mode, a continuous wave Doppler (CW) mode, and a motion (M) mode, and the scanning method indicates any one of scanning methods, such as an electronic sector scanning method, an electronic linear scanning method, and an electronic convex scanning method.

Further, the ultrasound transmission and reception control unit 15 controls the transmission and reception of ultrasonic waves by the transmitting and receiving unit 14 on the basis of ultrasound transmission and reception conditions corresponding to the operating state of the image display device 3 wirelessly transmitted from the image display device 3. Here, the ultrasound transmission and reception conditions include, for example, the number of times ultrasonic waves are transmitted and received per unit time, that is, a so-called scanning rate of ultrasonic waves. The operating state of the image display device 3 will be described below.

The signal processing unit 16 of the image information data generation unit 19 corrects the attenuation of the sound ray signal generated by the beam former 28 of the receiving unit 13 caused by a propagation distance according to the depth of the position where the ultrasonic waves are reflected and performs an envelope detection process on the sound ray signal to generate a signal which is tomographic image information related to the tissues in the subject.

The image processing unit 17 of the image information data generation unit 19 raster-converts the signal generated by the signal processing unit 16 into an image signal following a general television signal scanning method, performs various types of necessary image processing, such as brightness correction, gradation correction, sharpness correction, and color correction, on the generated image signal to generate an ultrasound image signal, and transmits the ultrasound image signal as image information data to the probe-side wireless communication unit 18.

The probe-side wireless communication unit 18 of the ultrasound probe 2 includes an antenna for transmitting and receiving radio waves and performs wireless communication with the display-device-side wireless communication unit 32 of the image display device 3. In this case, the probe-side wireless communication unit 18 modulates a carrier on the basis of the ultrasound image signal generated by the image processing unit 17 of the image information data generation unit 19 to generate a transmission signal and wirelessly transmits the generated transmission signal to the display-device-side wireless communication unit 32 of the image display device 3. For example, amplitude shift keying (ASK), phase shift keying (PSK), quadrature phase shift keying (QPSK), and 16 quadrature amplitude modulation (16QAM) are used as the carrier modulation method.

In addition, for example, the probe-side wireless communication unit 18 demodulates the transmission signal indicating the operating state of the image display device 3, which has been acquired by the operating state acquisition unit 40 of the image display device 3, which will be described below, and wirelessly transmitted by the display-device-side wireless communication unit 32 of the image display device 3, and outputs information indicating the operating state of the image display device 3 to the probe control unit 21.

The probe control unit 21 of the probe-side processor 25 controls each unit of the ultrasound probe 2 on the basis of, for example, a program stored in advance.

The battery 24 of the ultrasound probe 2 is provided in the ultrasound probe 2 and supplies power to each circuit of the ultrasound probe 2.

The communication control unit 20 of the probe-side processor 25 controls the probe-side wireless communication unit 18 such that the ultrasound image signal is transmitted with transmission radio field intensity set by the probe control unit 21.

The output format setting unit 22 of the probe-side processor sets the output format of the ultrasound image signal wirelessly transmitted to the image display device 3 on the basis of the operating state of the image display device 3. Here, examples of the output format of the ultrasound image signal include the compression ratio of the ultrasound image signal, a transfer rate in a case in which a transmission signal is wirelessly transmitted from the probe-side wireless communication unit 18 to the display-device-side wireless communication unit 32 of the image display device 3, and an image size in a case in which the ultrasound image signal is displayed as an ultrasound image on the display unit 34. Here, the transfer rate is the number of times the ultrasound image signal is wirelessly transmitted from the probe-side wireless communication unit 18 to the display-device-side wireless communication unit 32 per unit time. The operating state of the image display device 3 will be described below.

The display-device-side wireless communication unit 32 of the image display device 3 includes an antenna for transmitting and receiving radio waves and performs wireless communication with the probe-side wireless communication unit 18 of the ultrasound probe 2. In this case, the display-device-side wireless communication unit 32 of the image display device 3 receives, for example, the transmission signal wirelessly transmitted from the probe-side wireless communication unit 18 of the ultrasound probe 2 through the antenna, demodulates the received transmission signal, and outputs an ultrasound image signal.

Further, the display-device-side wireless communication unit 32 modulates a carrier on the basis of the information indicating the operating state of the image display device 3, which has been acquired by the operating state acquisition unit 40, to generate a transmission signal and wirelessly transmits the generated transmission signal to the probe-side wireless communication unit 18 of the ultrasound probe 2. As a carrier modulation method, for example, ASK, PSK, QPSK, and 16QAM are used as in the probe-side wireless communication unit 18 of the ultrasound probe 2.

The communication control unit 35 of the display-device-side processor 41 controls the display-device-side wireless communication unit 32 of the image display device 3 such that the reception of the transmission signal from the probe-side wireless communication unit 18 of the ultrasound probe 2 and the transmission of the transmission signal to the probe-side wireless communication unit 18 are performed.

The communication state detection unit 39 of the display-device-side processor 41 detects a wireless communication state between the probe-side wireless communication unit 18 of the ultrasound probe 2 and the display-device-side wireless communication unit 32 of the image display device 3. For example, in this case, the communication state detection unit 39 can detect, as the wireless communication state, the amount of data wirelessly communicated between the probe-side wireless communication unit 18 and the display-device-side wireless communication unit 32 per unit time, that is, a so-called data communication speed. Further, for example, the communication state detection unit 39 can detect, as the wireless communication state, the transfer rate of the ultrasound image signal from the probe-side wireless communication unit 18 to the display-device-side wireless communication unit 32.

The display control unit 33 of the display-device-side processor 41 performs predetermined processing on the ultrasound image signal demodulated by the display-device-side wireless communication unit 32 and displays an ultrasound image on the display unit 34 under the control of the main body control unit 36.

The main body control unit 36 of the display-device-side processor 41 controls each unit of the image display device 3 on the basis of the program stored in advance in, for example, the storage unit 38 and the operation of the user input through the operation unit 37.

The display unit 34 of the image display device 3 displays the image generated by the display control unit 33 and includes, for example, a display device such as a liquid crystal display (LCD).

The operation unit 37 of the image display device 3 is used by the user to perform an input operation and can be configured to comprise, for example, a keyboard, a mouse, a trackball, a touch pad, and a touch panel.

The storage unit 38 of the image display device 3 stores, for example, an operation program for the image display device 3. The following can be used as the storage unit 38: a recording medium, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), or a sever.

Here, the probe-side processor 25 including the transmitting and receiving unit 14, the ultrasound transmission and reception control unit 15, the probe-side wireless communication unit 18, the image information data generation unit 19, the communication control unit 20, the probe control unit 21, and the output format setting unit 22 in the ultrasound probe 2 and the display-device-side processor 41 including the display control unit 33, the communication control unit 35, the main body control unit 36, the communication state detection unit 39, and the operating state acquisition unit 40 in the image display device 3 are implemented by a central processing unit (CPU) and a control program for causing the CPU to perform various processes. However, the processors may be implemented by a field programmable gate array (FPGA), a digital signal processor (DSP), an application specific integrated circuit (ASIC), a graphics processing unit (GPU), other integrated circuits (ICs), or combinations thereof.

Some or all of the transmitting and receiving unit 14, the ultrasound transmission and reception control unit 15, the probe-side wireless communication unit 18, the image information data generation unit 19, the communication control unit 20, the probe control unit 21, and the output format setting unit 22 of the probe-side processor 25 may be integrated into, for example, one CPU. Similarly, some or all of the display control unit 33, the communication control unit 35, the main body control unit 36, the communication state detection unit 39, and the operating state acquisition unit 40 of the display-device-side processor 41 may be integrated into, for example, one CPU.

The operating state acquisition unit 40 of the display-device-side processor 41 acquires information indicating the operating state of the image display device 3 and transmits the acquired information to the display-device-side wireless communication unit 32. For example, in a case in which the display-device-side processor 41 is configured by a CPU or includes a CPU, the operating state acquisition unit 40 can acquire the configuration of the CPU, the processing capability of the CPU, and the clock frequency of the CPU as the operating state of the image display device 3. Here, the configuration of the CPU means, for example, the number of cores provided in the CPU. The processing capability of the CPU means, for example, the number of threads that can be processed by the CPU at the same time.

Further, for example, the operating state acquisition unit 40 may acquire, as the operating state of the image display device 3, the resolution of the display unit 34, the refresh rate of the display unit 34, and the wireless communication state between the ultrasound probe 2 and the image display device 3 detected by the communication state detection unit 39. Here, the refresh rate of the display unit 34 indicates the number of times the display unit 34 can update display per unit time. For example, each display device used as the display unit 34 has a unique refresh rate.

In addition, the operating state acquisition unit 40 can acquire information indicating at least one operating state among the plurality of types of operating states.

However, the processing capability of the display-device-side processor 41 required for displaying an ultrasound image on the display unit 34 of the image display device 3 changes depending on the operating state of the image display device 3. In the ultrasound system according to the related art in which the ultrasound probe and the image display device are connected to each other by wireless communication, in a case in which the sufficient processing capability of the display-device-side processor 41 is not obtained due to the operating state of the image display device 3, the processing of the signal wirelessly transmitted from the ultrasound probe is delayed and it is sometimes difficult to normally display the ultrasound image.

In the ultrasound system 1 according to Embodiment 1 of the invention, the information indicating the operating state of the image display device 3 acquired by the operating state acquisition unit 40 of the display-device-side processor 41 is wirelessly transmitted to the ultrasound probe 2 and the ultrasound transmission and reception control unit 15 controls the transmission and reception of ultrasonic waves on the basis of the operating state of the image display device 3. In this case, the ultrasound transmission and reception control unit 15 controls the transmitting and receiving unit 14 such that, as at least one of the processing capability of the image display device 3 or the wireless communication state between the ultrasound probe 2 and the image display device 3 deteriorates, the scanning rate of the transmitting and receiving unit 14 is reduced, which makes it possible to reduce the number of ultrasound image signals generated per unit time in the image information data generation unit 19. Therefore, it is possible to reduce the amount of data per unit time wirelessly transmitted from the probe-side wireless communication unit 18 to the image display device 3. Further, it is possible to reduce the amount of data of the ultrasound image signal processed per unit time in the display-device-side processor 41.

As such, the ultrasound transmission and reception control unit 15 of the probe-side processor 25 controls the transmission and reception of ultrasonic waves according to the operating state of the image display device 3 such that the amount of data of the ultrasound image signal processed per unit time in the display-device-side processor 41 is reduced. Therefore, it is possible to normally display an ultrasound image on the display unit 34, regardless of the processing capability of the display-device-side processor 41.

In addition, in the ultrasound system 1 according to the invention, the output format setting unit 22 sets the output format of the ultrasound image signal according to the operating state of the image display device 3. In a case in which the output format setting unit 22 sets the output format such that the amount of data of the ultrasound image signal is reduced by, for example, increasing the compression ratio of the ultrasound image signal, the amount of data of the ultrasound image signal processed in the display-device-side processor 41 is reduced.

Further, for example, in a case in which the ultrasound transmission and reception control unit 15 controls the transmitting and receiving unit 14 such that the scanning rate of the transmitting and receiving unit 14 is reduced and the output format setting unit 22 sets the output format such that the transfer rate of the ultrasound image signal from the probe-side wireless communication unit 18 to the display-device-side wireless communication unit 32 is reduced, the amount of data processed per unit time in the display-device-side processor 41 is reduced.

As described above, in the ultrasound system 1 according to Embodiment 1 of the invention, the amount of data processed by the display-device-side processor 41 per unit time is reduced according to the operating state of the image display device 3. Therefore, it is possible to normally display an ultrasound image, regardless of the operating state of the image display device 3.

The ultrasound probe 2 of the ultrasound system 1 according to Embodiment 1 comprises the ultrasound transmission and reception control unit 15 and the output format setting unit 22. However, the ultrasound probe 2 may comprise only one of the ultrasound transmission and reception control unit 15 and the output format setting unit 22. In this case, it is also possible to reduce the amount of data processed by the display-device-side processor 41 per unit time according to the operating state of the image display device 3. Therefore, it is possible to normally display an ultrasound image on the display unit 34, regardless of the operating state of the image display device 3.

Embodiment 2

Figure 3:
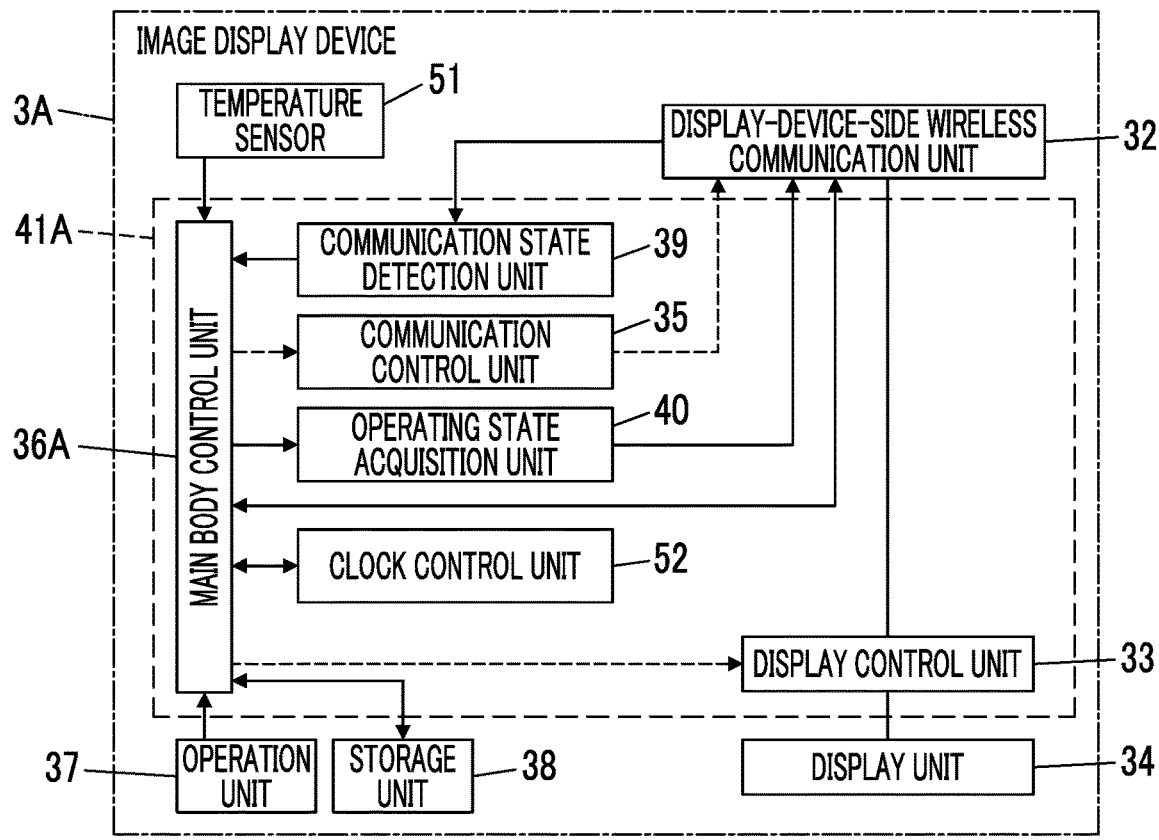
FIG. 3 is a block diagram illustrating a configuration of an image display device according to Embodiment 2 of the invention.

An ultrasound system according to Embodiment 2 comprises an image display device 3A illustrated in FIG. 3, instead of the image display device 3 of the ultrasound system 1 according to Embodiment 1 illustrated in FIG. 1. The image display device 3A according to Embodiment 2 is different from the image display device 3 according to Embodiment 1 illustrated in FIG. 1 in that it comprises a main body control unit 36A instead of the main body control unit 36 and further comprises a temperature sensor 51 and a clock control unit 52.

As illustrated in FIG. 3, in the image display device 3A, the main body control unit 36A is connected to the display control unit 33, the communication control unit 35, the operation unit 37, the storage unit 38, the communication state detection unit 39, the operating state acquisition unit 40, the temperature sensor 51, and the clock control unit 52. In this case, the main body control unit 36A and the clock control unit 52 are connected such that information can be bidirectionally transmitted and received. The display control unit 33, the communication control unit 35, the main body control unit 36A, the communication state detection unit 39, the operating state acquisition unit 40, and the clock control unit 52 form a display-device-side processor 41A.

Further, a portion or all of the display-device-side processor 41A of the image display device 3A is configured by a CPU.

The temperature sensor 51 of the image display device 3A is provided in the image display device 3A and detects the temperature of the image display device 3A. For example, as the temperature sensor 51, the following are used: a thermistor that detects the temperature on the basis of a change in electric resistance according to the temperature; and a thermocouple that detects the temperature on the basis of a thermoelectromotive force between two kinds of metal.

The clock control unit 52 of the display-device-side processor 41A controls the clock frequency of the CPU included in the display-device-side processor 41A according to the temperature of the image display device 3A detected by the temperature sensor 51. Here, in general, as the clock frequency of the CPU becomes higher, the amount of heat generated in the CPU becomes larger. Therefore, the clock control unit 52 reduces the clock frequency of the CPU as the temperature detected by the temperature sensor 51 increases to suppress the generation of heat in the CPU and to prevent an increase in the temperature of the image display device 3A.

In this case, the operating state acquisition unit 40 of the display-device-side processor 41A can acquire, as the operating state of the image display device 3A, the clock frequency of the CPU controlled by the clock control unit 52 in addition to, for example, the configuration of the CPU, the processing capability of the CPU, the resolution of the display unit 34, and the refresh rate of the display unit 34 exemplified in Embodiment 1.

Here, in a case in which the clock frequency of the CPU is reduced in order to prevent an increase in the temperature of the image display device 3A, the processing capability of the display-device-side processor 41A is also reduced. However, in Embodiment 2 of the invention, similarly to the aspect described in Embodiment 1, the operating state acquisition unit 40 of the display-device-side processor 41A transmits the operating state of the image display device 3A to the ultrasound probe 2 through the display-device-side wireless communication unit 32.

In this case, the ultrasound transmission and reception control unit 15 of the probe-side processor 25 illustrated in FIG. 1 controls the transmitting and receiving unit 14 such that the scanning rate of the transmitting and receiving unit 14 is reduced according to the operating state of the image display device 3A acquired by the operating state acquisition unit 40, thereby reducing the number of ultrasound image signals generated per unit time in the image information data generation unit 19. Further, the output format setting unit 22 of the ultrasound probe 2 sets the output format of the ultrasound image signal such that the amount of data of the ultrasound image signal is reduced according to the operating state of the image display device 3A. Therefore, according to the ultrasound system of Embodiment 2 of the invention, similarly to the ultrasound system 1 according to Embodiment 1, it is possible to normally display an ultrasound image, regardless of the operating state of the image display device 3A.

Embodiment 3

Figure 4:
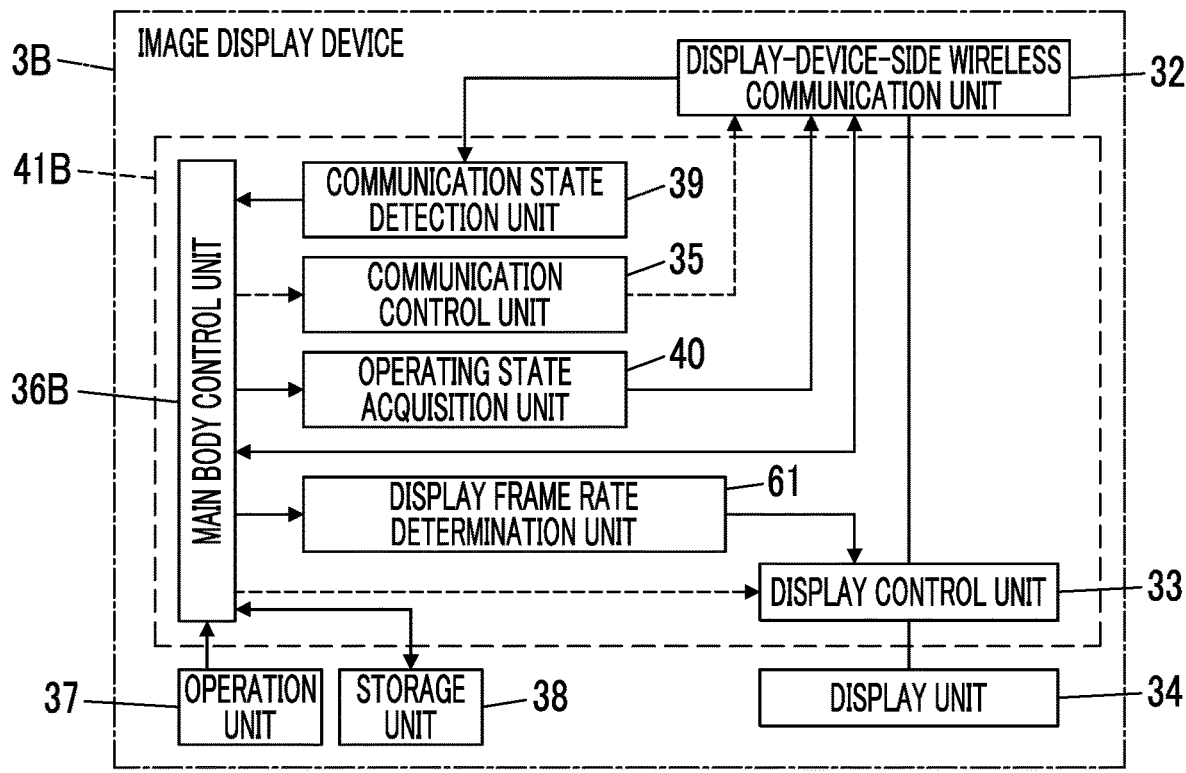
FIG. 4 is a block diagram illustrating a configuration of an image display device according to Embodiment 3 of the invention.

An ultrasound system according to Embodiment 3 comprises an image display device 3B illustrated in FIG. 4, instead of the image display device 3 of the ultrasound system 1 according to Embodiment 1 illustrated in FIG. 1. The image display device 3B according to Embodiment 2 is different from the image display device 3 according to Embodiment 1 illustrated in FIG. 1 in that it comprises a main body control unit 36B instead of the main body control unit 36 and further comprises a display frame rate determination unit 61.

As illustrated in FIG. 4, in the image display device 3B, the main body control unit 36B is connected to the display control unit 33, the communication control unit 35, the operation unit 37, the storage unit 38, the communication state detection unit 39, the operating state acquisition unit 40, and the display frame rate determination unit 61. The display control unit 33, the communication control unit 35, the main body control unit 36B, the communication state detection unit 39, the operating state acquisition unit 40, and the display frame rate determination unit 61 form a display-device-side processor 41B.

However, in the ultrasound system according to the related art in which the ultrasound probe and the image display device are connected by wireless communication, the number of ultrasound images transmitted to the display unit per unit time, that is, the transmission rate of the ultrasound images to the display unit may be less than the display frame rate of the display unit comprised in the image display device and may vary due to, for example, a reduction in the processing capability of the image display device and the deterioration of the wireless communication state between the ultrasound probe and the image display device.

In this case, the number of frames transmitted to the display unit per unit time is less than the number of frames displayed on the display unit per unit time, and the number of frames transmitted to the display unit per unit time varies. Therefore, there is a concern that the time interval between the frames displayed on the display unit will vary. The variation in the time interval between the frames in the display unit is a factor that prevents a user, such as a doctor who visually recognizes the ultrasound image displayed on the display unit and makes a diagnosis, from making a stable diagnosis.

The display frame rate determination unit 61 of the display-device-side processor 41B determines the display frame rate of the ultrasound images in the display unit 34 on the basis of at least the wireless communication state between the probe-side wireless communication unit 18 of the ultrasound probe 2 and the display-device-side wireless communication unit 32 of the image display device 3B which has been detected by the communication state detection unit 39. In this case, the display frame rate determination unit 61 determines the display frame rate of the display unit 34 such that the transmission rate of the ultrasound image to the display unit 34 is greater than the display frame rate of the display unit 34.

For example, in a case in which the communication state detection unit 39 detects the transfer rate of the transmission signal from the probe-side wireless communication unit 18 to the display-device-side wireless communication unit 32, the display frame rate determination unit 61 determines, as the display frame rate, a value obtained by multiplying the transfer rate detected by the communication state detection unit 39 by a predetermined percentage. As a specific example, the display frame rate determination unit 61 can determine, as the display frame rate, a rate that is about 70% of the transfer rate detected by the communication state detection unit 39.

The display control unit 33 transmits image data that can be displayed to the display unit 34 under the control of the main body control unit 36B such that the ultrasound images are displayed at the display frame rate determined by the display frame rate determination unit 61.

As described above, according to the ultrasound system of Embodiment 3, the display frame rate of the display unit 34 is determined on the basis of at least the wireless communication state between the ultrasound probe 2 and the image display device 3B such that the transmission rate of the ultrasound image to the display unit 34 is greater than the display frame rate of the display unit 34. Therefore, the ultrasound image is displayed on the display unit 34 with a sufficient margin and it is possible to prevent a variation in the time interval between the frames in the display unit 34.

Further, in Embodiment 3, the example in which the display frame rate determination unit 61 determines the display frame rate of the display unit 34 on the basis of only the transfer rate detected by the communication state detection unit 39 has been described. However, the method for determining the display frame rate is not limited thereto. For example, the display frame rate determination unit 61 can determine the display frame rate of the display unit 34, considering the generation rate of the ultrasound image signal in the image information data generation unit 19 of the probe-side processor 25 and the processing capability of the image display device 3B illustrated in FIG. 1, in addition to the wireless communication state between the ultrasound probe 2 and the image display device 3B.

In this case, for example, the display frame rate determination unit 61 can determine, as the display frame rate of the display unit 34, a minimum value among a first display frame rate candidate value based on the wireless communication state between the ultrasound probe 2 and the image display device 3B, a second display frame rate candidate value based on the generation rate of the ultrasound image signal in the ultrasound probe 2, and a third display frame rate candidate value based on the processing capability of the image display device 3B.

For example, the display frame rate determination unit 61 can set a value calculated by multiplying the transfer rate of the transmission signal detected by the communication state detection unit 39 of the display-device-side processor 41B by a predetermined percentage as the first display frame rate candidate value, set the generation rate of the ultrasound image signal in the image information data generation unit 19 of the probe-side processor 25 as the second display frame rate candidate value, and set an image processing rate at which an image that can be displayed on the display unit 34 is generated in the image display device 3B as the third display frame rate candidate value. Here, the image processing rate of the image display device 3B which is the third display frame rate candidate value includes the influence of, for example, the processing capability of the display-device-side wireless communication unit 32 related to the demodulation of the transmission signal and the processing capability of the display control unit 33 related to the generation of the image data that can be displayed.

Further, in a case in which the image display device 3B comprises the temperature sensor 51 illustrated in FIG. 3, in the acquisition of the third display frame rate candidate value, the display frame rate determination unit 61 may store, for example, the relationship between the operating time and the temperature of the image display device 3B and the relationship between the temperature and the image processing rate of the image display device 3B in advance, may predict the image processing rate in a case in which the image display device 3B is operated for about 5 minutes on the basis of the current temperature of the image display device 3B measured by the temperature sensor 51, and may set the image processing rate as the third display frame rate candidate value.

As such, the display frame rate of the display unit 34 is determined on the basis of the first display frame rate candidate value, the second display frame rate candidate value, and the third display frame rate candidate value, which makes it possible to display an ultrasound image on the display unit 34 with a further margin and to prevent a variation in the time interval between the frames in the display unit 34.

Embodiment 4

Figure 5:
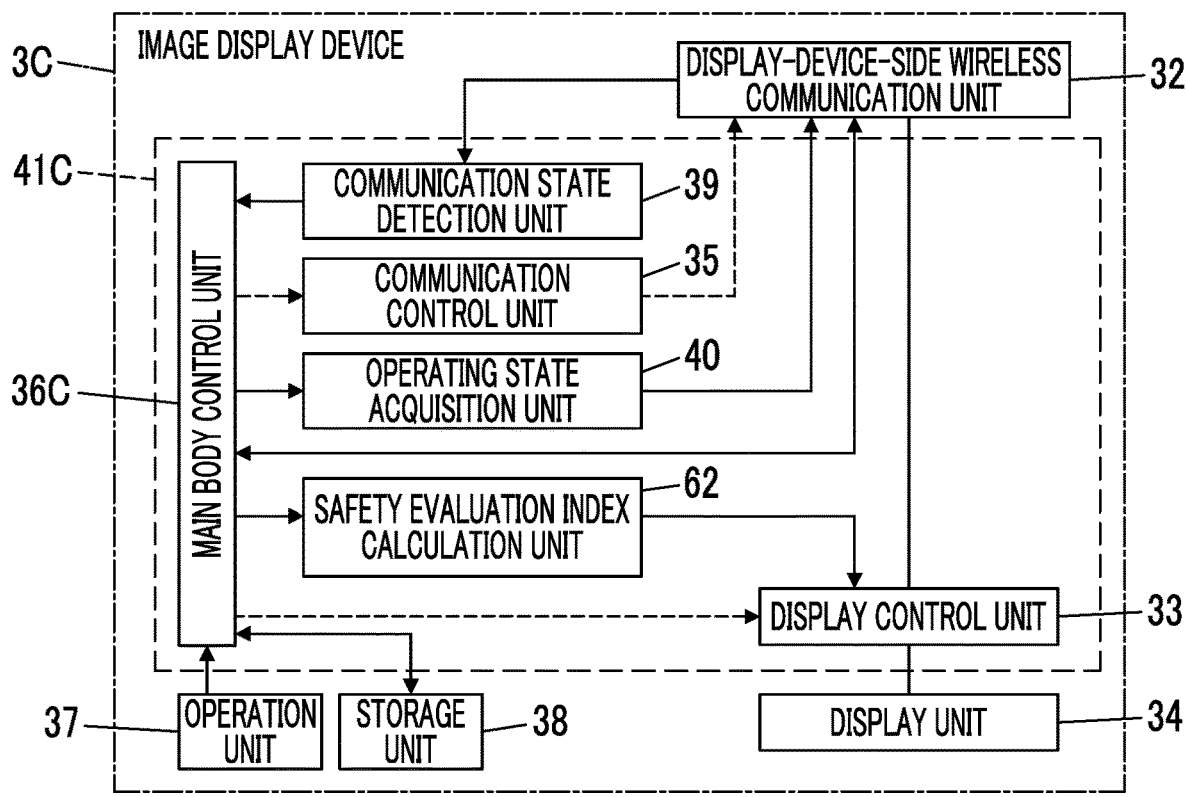
FIG. 5 is a block diagram illustrating a configuration of an image display device according to Embodiment 4 of the invention.

An ultrasound system according to Embodiment 4 comprises an image display device 3C illustrated in FIG. 5, instead of the image display device 3 of the ultrasound system 1 according to Embodiment 1 illustrated in FIG. 1. The image display device 3C according to Embodiment 4 is different from the image display device 3 according to Embodiment 1 illustrated in FIG. 1 in that it comprises a main body control unit 36C, instead of the main body control unit 36, and further comprises a safety evaluation index calculation unit 62.

As illustrated in FIG. 5, in the image display device 3C, the main body control unit 36C is connected to the display control unit 33, the communication control unit 35, the communication state detection unit 39, the operating state acquisition unit 40, and the safety evaluation index calculation unit 62. Further, the display control unit 33, the communication control unit 35, the main body control unit 36C, the communication state detection unit 39, the operating state acquisition unit 40, and the safety evaluation index calculation unit 62 form a display-device-side processor 41C.

The safety evaluation index calculation unit 62 of the display-device-side processor 41C calculates a safety evaluation index on the basis of ultrasound transmission and reception conditions controlled by the ultrasound transmission and reception control unit 15 of the ultrasound probe 2 illustrated in FIG. 1 and displays the calculated safety evaluation index on the display unit 34. In this case, first, the ultrasound probe 2 wirelessly transmits, to the image display device 3C, a notification that the transmission and reception of ultrasonic waves by the transmitting and receiving unit 14 are controlled on the basis of the ultrasound transmission and reception conditions corresponding to the operating state of the image display device 3C. After the wirelessly transmitted notification is received by the safety evaluation index calculation unit 62, the safety evaluation index is calculated. The calculated safety evaluation index is displayed on the display unit 34.

Here, the ultrasound transmission and reception conditions controlled by the ultrasound transmission and reception control unit 15 include, for example, the intensity of the ultrasonic waves transmitted from the transducer array 11, that is, the level of the voltage of the driving signal transmitted by the transmitting unit 12, the center frequency of the ultrasonic waves, and the amplification factor of the reception signal, in addition to the scanning rate of the transmitting and receiving unit 14.

Further, the safety evaluation index is an index for evaluating safety against the influence of ultrasonic waves on a living body and includes, for example, a mechanical index (MI) value for evaluating the safety of a mechanical action, such as the radiation pressure and vibration of the ultrasonic waves in the living body, and a thermal index (TI) value for evaluating safety against a living body heating action caused by the absorption of the energy of the ultrasonic waves in the living body.

For example, in a case in which the MI value is calculated as the safety evaluation index, the safety evaluation index calculation unit 62 can divide the maximum negative sound pressure of the ultrasonic waves considering attenuation in the living body by the square root of the center frequency of the ultrasonic waves transmitted from the transducer array 11 to calculate the MI value. In addition, in a case in which the TI value is calculated as the safety evaluation index, the safety evaluation index calculation unit 62 can divide the output intensity of the ultrasonic waves in the living body by the output intensity of the ultrasonic waves required to increase the temperature of the living tissues by 1° C. to calculate the TI value.

The user can check the value of the safety evaluation index displayed on the display unit 34 to understand the influence of the ultrasonic waves transmitted from the transducer array 11 on the inside of the subject.

As described above, according to the ultrasound system of Embodiment 4, even in a case in which the ultrasound transmission and reception conditions are newly set by the ultrasound transmission and reception control unit 15 of the probe-side processor 25 in order to normally display an ultrasound image on the display unit 34 regardless of the operating state of the image display device 3C, the safety evaluation index corresponding to the set ultrasound transmission and reception conditions is displayed on the display unit 34. Therefore, the user can accurately understand the influence of the ultrasonic waves transmitted from the transducer array 11 on the inside of the subject.

Embodiment 5

Figure 6:
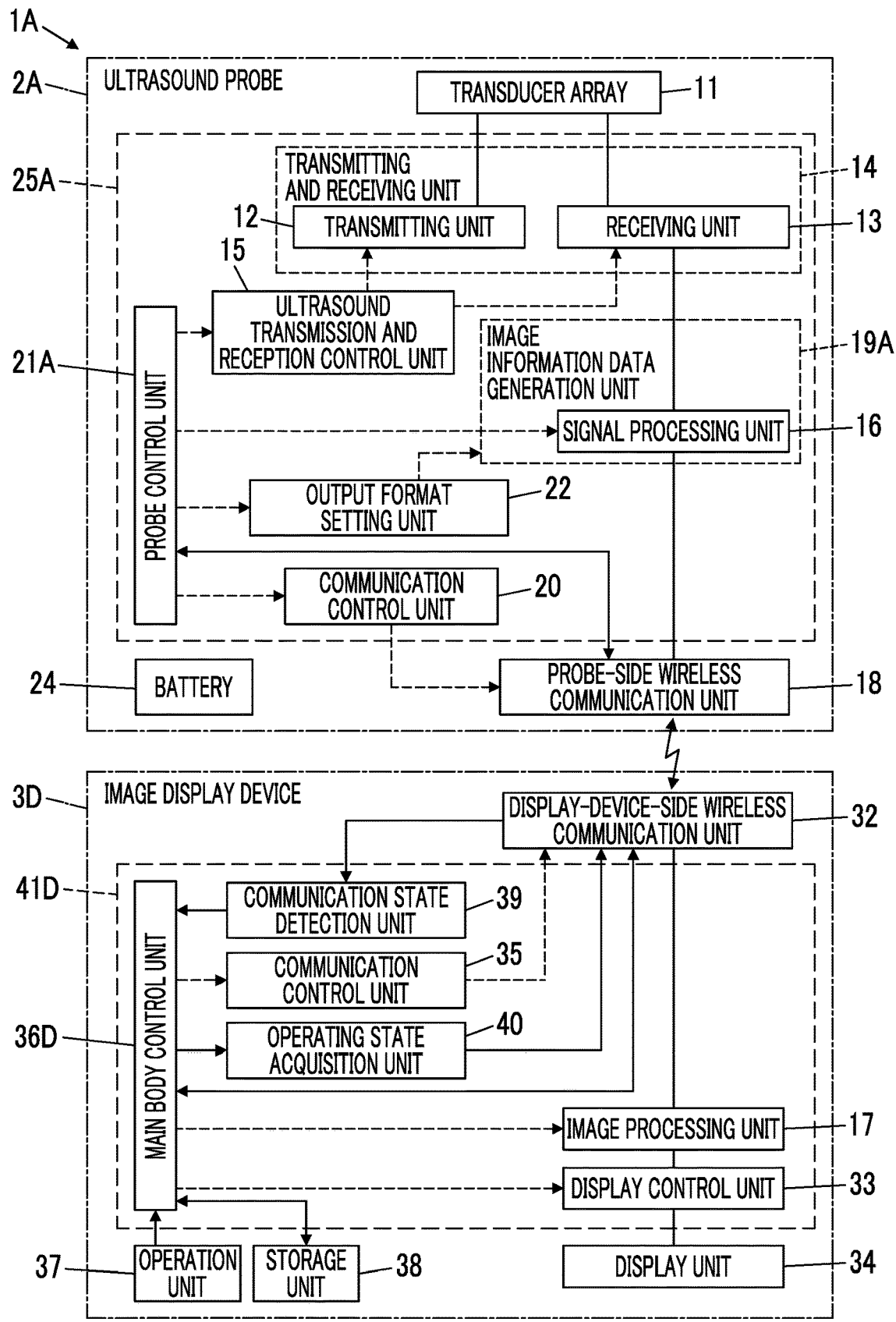
FIG. 6 is a block diagram illustrating a configuration of an ultrasound system according to Embodiment 5 of the invention.

FIG. 6 illustrates the configuration of an ultrasound system 1A according to Embodiment 5. The ultrasound system 1A is different from the ultrasound system 1 according to Embodiment 1 illustrated in FIG. 1 in that it comprises an ultrasound probe 2A instead of the ultrasound probe 2 and comprises an image display device 3D instead of the image display device 3.

The ultrasound probe 2A of the ultrasound system 1A is different from the ultrasound probe 2 illustrated in FIG. 1 in that it comprises an image information data generation unit 19A having only the signal processing unit 16 instead of the image information data generation unit 19 having the signal processing unit 16 and the image processing unit 17 and comprises a probe control unit 21A instead of the probe control unit 21. The ultrasound probe 2A according to Embodiment 5 has the same configuration as the ultrasound probe 2 according to Embodiment 1 except the image information data generation unit 19A and the probe control unit 21A.

In the ultrasound probe 2A, the signal processing unit 16 is directly connected to the probe-side wireless communication unit 18. Further, the transmitting unit 12, the receiving unit 13, the ultrasound transmission and reception control unit 15, the signal processing unit 16, the communication control unit 20, the probe control unit 21A, and the output format setting unit 22 form a probe-side processor 25A.

The image display device 3D is different from the image display device 3 according to Embodiment 1 illustrated in FIG. 1 in that the image processing unit 17 is connected between the display-device-side wireless communication unit 32 and the display control unit 33 and a main body control unit 36D is provided instead of the main body control unit 36. The image display device 3D has the same configuration as the image display device 3 according to Embodiment 1 except the image processing unit 17 and the main body control unit 36D.

The image processing unit 17, the display control unit 33, the communication control unit 35, the main body control unit 36D, the communication state detection unit 39, and the operating state acquisition unit 40 form a display-device-side processor 41D. The image processing unit 17 of the image display device 3D is the same as the image processing unit 17 comprised in the ultrasound probe 2 according to Embodiment 1.

The signal processing unit 16 of the image information data generation unit 19A corrects the attenuation of the sound ray signal generated by the beam former 28 of the receiving unit 13 caused by a propagation distance according to the depth of the position where the ultrasonic waves are reflected and performs an envelope detection process on sound ray signal to generate, as image information data, a signal that is tomographic image information related to the tissues in the subject.

The probe-side wireless communication unit 18 of the ultrasound probe 2A modulates a carrier on the basis of the signal generated by the signal processing unit 16 of the image information data generation unit 19A to generate a transmission signal and wirelessly transmits the generated transmission signal to the display-device-side wireless communication unit 32 of the image display device 3D.

The display-device-side wireless communication unit 32 of the image display device 3D demodulates the transmission signal wirelessly transmitted from the ultrasound probe 2A to acquire the signal generated by the signal processing unit 16 of the image information data generation unit 19A and transmits the signal to the image processing unit 17 of the display-device-side processor 41D.

The image processing unit 17 of the display-device-side processor 41D raster-converts the signal transmitted from the display-device-side wireless communication unit 32 into an image signal following the general television signal scanning method, performs various types of necessary image processing, such as brightness correction, gradation correction, sharpness correction, and color correction, on the generated image signal to generate an ultrasound image signal, and transmits the generated ultrasound image signal to the display control unit 33. The ultrasound image signal transmitted to the display control unit 33 is converted into image data that can be displayed by the display control unit 33 and is then displayed on the display unit 34.

The operating state acquisition unit 40 of the display-device-side processor 41D acquires information indicating the operating state of the image display device 3D and transmits the acquired information to the display-device-side wireless communication unit 32.

In a case in which the information indicating the operating state of the image display device 3D is transmitted to the display-device-side wireless communication unit 32, the display-device-side wireless communication unit 32 modulates the carrier on the basis of the information to generate a transmission signal and wirelessly transmits the generated transmission signal to the probe-side wireless communication unit 18.

The transmission signal wirelessly transmitted from the display-device-side wireless communication unit 32 to the probe-side wireless communication unit 18 is demodulated into the information indicating the operating state of the image display device 3D by the probe-side wireless communication unit 18 and is transmitted to the probe control unit 21A.

Then, the ultrasound transmission and reception control unit 15 sets ultrasound transmission and reception conditions according to the operating state of the image display device 3D and controls the transmitting and receiving unit 14 on the basis of the set ultrasound transmission and reception conditions. In this case, for example, the ultrasound transmission and reception control unit 15 controls the transmitting and receiving unit 14 such that the scanning rate of the transmitting and receiving unit 14 is reduced according to the operating state of the image display device 3D. Therefore, it is possible to reduce the generation rate of the ultrasound image signal in the image processing unit 17 of the display-device-side processor 41D and to reduce the amount of data processed per unit time in the display-device-side processor 41D.

The output format setting unit 22 of the probe-side processor 25A sets the output format of the signal generated by the signal processing unit 16 according to the operating state of the image display device 3D. In this case, the output format setting unit 22 can set the output format such that the amount of data of the signal is reduced, for example, by compressing the signal generated by the signal processing unit 16. Therefore, the amount of data processed in the display-device-side processor 41D is reduced.

Further, for example, in a case in which the ultrasound transmission and reception control unit 15 controls the transmitting and receiving unit 14 such that the scanning rate of the transmitting and receiving unit 14 is reduced and the output format setting unit 22 sets the output format such that the transfer rate of the transmission signal from the probe-side wireless communication unit 18 to the display-device-side wireless communication unit 32 is reduced, it is possible to reduce the amount of data processed per unit time in the display-device-side processor 41.

As described above, even in a case in which the image processing unit 17 is not provided in the ultrasound probe 2A, but is provided in the image display device 3D as in the ultrasound system 1A according to Embodiment 5, the amount of data processed by the display-device-side processor 41D per unit time is reduced according to the operating state of the image display device 3D as in the ultrasound system 1 according to Embodiment 1. Therefore, it is possible to normally display an ultrasound image, regardless of the operating state of the image display device 3D.

In the above-described Embodiments 1 to 4, the ultrasound image signal which has been subjected to the attenuation correction and the envelope detection process by the signal processing unit 16 of the image information data generation unit 19 and then subjected to raster conversion by the image processing unit 17 is wirelessly transmitted as the image information data from the probe-side wireless communication unit 18 to the image display device 3 or the image display devices 3A to 3C. In Embodiment 5, the signal subjected to the attenuation correction and the envelope detection process by the signal processing unit 16 of the image information data generation unit 19A is wirelessly transmitted as the image information data from the probe-side wireless communication unit 18 to the image display device 3D. As such, it is preferable that the image information data wirelessly transmitted from the ultrasound probe 2 to the image display devices 3 and 3A to 3C and the image information data wirelessly transmitted from the ultrasound probe 2A to the image display device 3D are signals after detection. However, the image information data is not limited to the signal after detection.

In the image display devices 3, 3A, 3B, 3C, and 3D according to the above-described Embodiments 1 to 5, a touch sensor may be combined with the display unit 34 and may be used as the operation unit 37. In this case, the ultrasound system 1 according to Embodiment 1, the ultrasound systems according to Embodiments 2 to 4, and the ultrasound system 1A according to Embodiment 5 are very effective for an outdoor diagnosis during, for example, emergency treatment.

EXPLANATION OF REFERENCES 1, 1A: ultrasound system
2, 2A: ultrasound probe
3, 3A, 3B, 3C, 3D: image display device
11: transducer array
12: transmitting unit
13: receiving unit
14: transmitting and receiving unit 15: ultrasound transmission and reception control unit
16: signal processing unit
17: image processing unit
18: probe-side wireless communication unit
19, 19A: image information data generation unit
20: communication control unit
21, 21A: probe control unit
22: output format setting unit
24: battery
25, 25A: probe-side processor
26: amplification unit
27: AD conversion unit
28: beam former
32: display-device-side wireless communication unit
33: display control unit
34: display unit
35: communication control unit
36, 36A, 36B, 36C, 36D: main body control unit
37: operation unit
38: storage unit
39: communication state detection unit
40: operating state acquisition unit
41, 41A, 41B, 41C, 41D: display-device-side processor
51: temperature sensor
52: clock control unit
61: display frame rate determination unit
62: safety evaluation index calculation unit.

What is claimed is:

1. An ultrasound system comprising:
an ultrasound probe; and
an image display device,
wherein the ultrasound probe includes:
a transducer array;
a first processor configured to:
transmit ultrasonic waves from the transducer array,
generate a sound ray signal on the basis of a reception signal acquired by the transducer array, and
generate image information data on the basis of the sound ray signal; and
a first wireless communication device configured to wirelessly transmit the image information data generated by the first processor to the image display device;
wherein the image display device includes:
a display monitor configured to display an ultrasound image on the basis of the image information data wirelessly transmitted from the ultrasound probe;
a second processor including a central processing unit, configured to:
acquire at least one of a configuration of the central processing unit or a resolution of the display monitor, as an operating state of the image display device; and
a second wireless communication device configured to wirelessly transmit the operating state of the image display device acquired by the second processor to the ultrasound probe; and
wherein the first processor in the ultrasound probe is further configured to perform at least one of
controlling transmission and reception of the ultrasonic waves by the first processor in the ultrasound probe such that a scanning rate of the ultrasonic wave is reduced on the basis of the operating state of the image display device and
setting an output format of the image information data to be wirelessly transmitted from the ultrasound probe to the image display device such that the amount of data of the image information data is reduced on the basis of the operating state of the image display device.

2. The ultrasound system according to claim 1,
wherein the image display device includes a temperature sensor,
the second processor in the image display device is further configured to control the clock frequency of the central processing unit according to a temperature detected by the temperature sensor, and
the operating state of the image display device is the clock frequency of the central processing unit controlled by the second processor in the image display device.

3. The ultrasound system according to claim 2,
wherein the second processor in the image display device is further configured to
calculate a safety evaluation index on the basis of ultrasound transmission and reception conditions controlled by the first processor in the ultrasound probe and
display the safety evaluation index on the display monitor,
the first wireless communication device of the ultrasound probe is further configured to wirelessly transmit, to the image display device, a notification that the transmission and reception of the ultrasonic waves by the first processor in the ultrasound probe are controlled on the basis of the ultrasound transmission and reception conditions corresponding to the operating state of the image display device wirelessly transmitted from the image display device, and
the second processor in the image display device is further configured to
calculate the safety evaluation index and
display the safety evaluation index on the display monitor after receiving the notification wirelessly transmitted from the ultrasound probe.

4. The ultrasound system according to claim 2,
wherein the image information data is a signal obtained by performing attenuation correction according to a depth of a reflection position of the ultrasonic waves and an envelope detection process on the sound ray signal generated by the first processor in the ultrasound probe.

5. The ultrasound system according to claim 2,
wherein the image information data is an ultrasound image signal obtained by performing attenuation correction according to a depth of a reflection position of the ultrasonic waves and an envelope detection process on the sound ray signal generated by the first processor in the ultrasound probe and converting the sound ray signal according to a predetermined image display method.

6. The ultrasound system according to claim 1,
wherein the second processor in the image display device is further configured to detect a wireless communication state between the ultrasound probe and the image display device, and
the operating state of the image display device is the wireless communication state detected by the processor in the image display device.

7. The ultrasound system according to claim 6,
wherein the second processor in the image display device is further configured to determine a display frame rate on the basis of at least the wireless communication state, and the display monitor is further configured to display the ultrasound image on the basis of the display frame rate determined by the processor in the image display device.

8. The ultrasound system according to claim 7,
wherein the second processor in the image display device is further configured to
calculate a safety evaluation index on the basis of ultrasound transmission and reception conditions controlled by the first processor in the ultrasound probe and
display the safety evaluation index on the display monitor,
the first wireless communication device of the ultrasound probe is further configured to wirelessly transmit, to the image display device, a notification that the transmission and reception of the ultrasonic waves by the first processor in the ultrasound probe are controlled on the basis of the ultrasound transmission and reception conditions corresponding to the operating state of the image display device wirelessly transmitted from the image display device, and
the second processor in the image display device is further configured to
calculate the safety evaluation index and
display the safety evaluation index on the display monitor after receiving the notification wirelessly transmitted from the ultrasound probe.

9. The ultrasound system according to claim 6,
wherein the second processor in the image display device is further configured to
calculate a safety evaluation index on the basis of ultrasound transmission and reception conditions controlled by the first processor in the ultrasound probe and
display the safety evaluation index on the display monitor,
the first wireless communication device of the ultrasound probe is further configured to wirelessly transmit, to the image display device, a notification that the transmission and reception of the ultrasonic waves by the first processor in the ultrasound probe are controlled on the basis of the ultrasound transmission and reception conditions corresponding to the operating state of the image display device wirelessly transmitted from the image display device, and
the second processor in the image display device is further configured to
calculate the safety evaluation index and
display the safety evaluation index on the display monitor after receiving the notification wirelessly transmitted from the ultrasound probe.

10. The ultrasound system according to claim 6,
wherein the image information data is a signal obtained by performing attenuation correction according to a depth of a reflection position of the ultrasonic waves and an envelope detection process on the sound ray signal generated by the first processor in the ultrasound probe.

11. The ultrasound system according to claim 6,
wherein the image information data is an ultrasound image signal obtained by performing attenuation correction according to a depth of a reflection position of the ultrasonic waves and an envelope detection process on the sound ray signal generated by the first processor in the ultrasound probe and converting the sound ray signal according to a predetermined image display method.

12. The ultrasound system according to claim 1,
wherein the second processor in the image display device is further configured to
calculate a safety evaluation index on the basis of ultrasound transmission and reception conditions controlled by the first processor in the ultrasound probe and
display the safety evaluation index on the display monitor,
the first wireless communication device of the ultrasound probe is further configured to wirelessly transmit, to the image display device, a notification that the transmission and reception of the ultrasonic waves by the first processor in the ultrasound probe are controlled on the basis of the ultrasound transmission and reception conditions corresponding to the operating state of the image display device wirelessly transmitted from the image display device, and
the second processor in the image display device is further configured to
calculate the safety evaluation index and
display the safety evaluation index on the display monitor after receiving the notification wirelessly transmitted from the ultrasound probe.

13. The ultrasound system according to claim 1,
wherein the image information data is a signal obtained by performing attenuation correction according to a depth of a reflection position of the ultrasonic waves and an envelope detection process on the sound ray signal generated by the first processor in the ultrasound probe.

14. The ultrasound system according to claim 1,
wherein the image information data is an ultrasound image signal obtained by performing attenuation correction according to a depth of a reflection position of the ultrasonic waves and an envelope detection process on the sound ray signal generated by the first processor in the ultrasound probe and converting the sound ray signal according to a predetermined image display method.

15. The ultrasound system according to claim 1,
wherein the first processor in the ultrasound probe is further configured to
direct the transducer array to transmit the ultrasonic waves and
generate the sound ray signal on the basis of the reception signal acquired by the transducer array.

16. A method of controlling an ultrasound system comprising an ultrasound probe and an image display device including a central processing unit, the method comprising:
generating a sound ray signal by directing a transducer array of the ultrasound probe to transmit and receive ultrasonic waves;
generating image information data on the basis of the generated sound ray signal;
wirelessly transmitting the generated image information data from the ultrasound probe to the image display device;
displaying an ultrasound image on a display monitor of the image display device on the basis of the image information data wirelessly transmitted from the ultrasound probe;
acquiring at least one of a configuration of the central processing unit or a resolution of the display monitor, as an operating state of the image display device;
wirelessly transmitting the operating state of the image display device from the image display device to the ultrasound probe; and
allowing the ultrasound probe to perform at least one of controlling of the transmission and reception of the ultrasonic waves such that a scanning rate of the ultrasonic wave is reduced on the basis of the operating state of the image display device and setting of an output format of the image information data to be wirelessly transmitted to the image display device such that the amount of data of the image information data is reduced on the basis of the operating state of the image display device.

\* \* \* \* \*